United States Patent
Shenoy et al.

(10) Patent No.: US 12,367,191 B1
(45) Date of Patent: Jul. 22, 2025

(54) SYSTEMS AND METHODS FOR SEARCHING DATABASE STRUCTURES USING SEMANTICALLY AND CATEGORICALLY SIMILAR QUERIES

(71) Applicant: UpToDate, Inc., Waltham, MA (US)

(72) Inventors: Siddharth Subhash Shenoy, Jersey City, NJ (US); Omar Bari, Brownstown, MI (US); Christian Aaron Hartman, East Greenwich, RI (US); Santosh Vinod Chapaneri, Maharashtra (IN); Atul Ujjwal, Pune (IN); Dishu Jindal, Waltham, MA (US)

(73) Assignee: UpToDate, Inc.

( * ) Notice: Subject to any disclaimer, the term of this patent is extended or adjusted under 35 U.S.C. 154(b) by 0 days.

(21) Appl. No.: 18/591,607

(22) Filed: Feb. 29, 2024

(51) Int. Cl.
*G06F 16/242* (2019.01)
*G06F 16/2455* (2019.01)
*G06F 16/248* (2019.01)

(52) U.S. Cl.
CPC .... *G06F 16/2428* (2019.01); *G06F 16/24552* (2019.01); *G06F 16/248* (2019.01)

(58) Field of Classification Search
CPC ........... G06F 16/2428; G06F 16/24552; G06F 16/248
See application file for complete search history.

(56) References Cited

U.S. PATENT DOCUMENTS

| | | | | |
|---|---|---|---|---|
| 6,169,986 B1 * | 1/2001 | Bowman | ............. | G06F 16/3325 707/999.005 |
| 8,943,036 B1 * | 1/2015 | Coudron | ............. | G06F 16/2428 707/706 |
| 9,009,146 B1 * | 4/2015 | Lopatenko | ................ | H04L 9/40 707/723 |
| 11,263,277 B1 | 3/2022 | Podgorny et al. | | |
| 12,124,497 B1 * | 10/2024 | Java | ................. | G06V 30/19147 |
| 12,229,174 B1 * | 2/2025 | Halder | ................ | G06F 16/3331 |
| 12,242,480 B1 * | 3/2025 | Martinez | ........... | G06F 16/24544 |

(Continued)

FOREIGN PATENT DOCUMENTS

WO 2024015323 A1 1/2024

OTHER PUBLICATIONS

International Search Report issued in corresponding Application No. PCT/US2025/016875, dated May 16, 2025, 0 pages.

*Primary Examiner* — Jorge A Casanova
(74) *Attorney, Agent, or Firm* — Morgan, Lewis & Bockius LLP (57) ABSTRACT

Systems and methods of searching content using one or more machine learning models are disclosed. In response to a user query request, a user query is received at a first user interface. One or more search terms are determined using a query parser based on the user query. One or more semantically similar queries are determined based on the one or more search terms. In accordance with a determination that the user query and the one or more semantically similar queries have not been previously searched, search for information related to the one or more search terms from one or more databases using the one or more machine learning models. An output to the user query is generated based on the information. The output includes at least a portion of the information and one or more citations associated with the information. The output is displayed at the first user interface.

20 Claims, 6 Drawing Sheets

(56) References Cited

U.S. PATENT DOCUMENTS

| | | | |
|---|---|---|---|
| 2014/0129535 A1* | 5/2014 | Riley | G06F 16/248 |
| | | | 707/706 |
| 2014/0222803 A1* | 8/2014 | Bowman | G06F 16/3334 |
| | | | 707/727 |
| 2015/0161255 A1* | 6/2015 | Battle | H04L 67/30 |
| | | | 707/706 |
| 2016/0246841 A1* | 8/2016 | Pesala | G06F 16/2365 |
| 2017/0039254 A1* | 2/2017 | Cady | G06F 16/248 |
| 2020/0250197 A1* | 8/2020 | Yang | G06F 16/24578 |
| 2020/0401629 A1* | 12/2020 | Lin | G06F 16/951 |
| 2021/0406260 A1 | 12/2021 | Sharifi et al. | |
| 2022/0035868 A1 | 2/2022 | Holmdahl et al. | |
| 2023/0119161 A1* | 4/2023 | Yadaw | G06F 40/30 |
| | | | 707/706 |
| 2024/0020538 A1* | 1/2024 | Socher | G06N 3/084 |
| 2024/0022577 A1* | 1/2024 | Fu | H04L 63/1425 |
| 2024/0193156 A1* | 6/2024 | Lin | G06F 18/214 |

\* cited by examiner

SYSTEMS AND METHODS FOR SEARCHING DATABASE STRUCTURES USING SEMANTICALLY AND CATEGORICALLY SIMILAR QUERIES

TECHNICAL FIELD

This application relates generally to database searching, and more particularly, to searching a database using a machine learning model.

BACKGROUND

Conventional database searching requires a user to already have knowledge of the target subject matter. For example, conventional methods of searching databases (e.g., PubMed or DailyMed) require specific medical keywords. These methods of searching require a substantial baseline knowledge in the target subject matter to retrieve information regarding the target subject matter. In other words, without a prerequisite amount of knowledge, traditional methods of searching databases are unlikely to output the desired information. One way, using traditional search methods, to eventually arrive at the desired information requires the user to perform multiple rounds of refinement of the search query. These rounds may be time intensive depending on the amount of knowledge in the target subject matter possessed by the user. Furthermore, an individual armed with the subject matter expertise may nonetheless be unable to search the database because of database specific search keywords (e.g., Boolean operators). Thus, traditional database searching techniques are not user friendly.

SUMMARY

In various embodiments, a system is disclosed. The system includes a non-transitory memory and a processor communicatively coupled to the non-transitory memory. The processor is configured to read a set of instructions to receive a user query in response to a user query request. The user query is received at a first user interface. The processor is further configured to determine one or more search terms from the user query using a query parser. The processor is further configured to determine one or more semantically similar queries meeting semantic similarity criteria. The determination of the one or more semantically similar queries is based on the one or more search terms of the user query. The processor is further configured to search for information related to the one or more search terms from one or more databases. The search uses one or more machine learning models. The processor is further configured to generate an output to the user query. The output is generated based on the information related to the one or more search terms. The output includes at least a portion of the information related to the one or more search terms. The output further includes one or more citations associated with the information related to the one or more search terms from the one or more databases. The processor is further configured to display the output to the user query at the first user interface.

In various embodiments, a computer implemented method is disclosed. The computer implemented method includes a step of receiving a user query in response to a user query request. The user query is received at a first user interface. The computer-implemented method further includes a step of determining one or more search terms from the user query using a query parser. The computer-implemented method further includes a step of determining one or more semantically similar queries based on the one or more search terms of the user query. The computer-implemented method further includes a step of searching for information related to the one or more search terms from one or more databases. The search uses one or more machine learning models. The computer-implemented method further includes a step of generating an output to the user query. The output is generated based on the information related to the one or more search terms. The output includes at least a portion of the information related to the one or more search terms. The output further includes one or more citations associated with the information related to the one or more search terms from the one or more databases. The computer-implemented method further includes a step of displaying the output to the user query at the first user interface.

In various embodiments, a non-transitory computer readable medium having instructions stored thereon is disclosed. The instructions, when executed by at least one processor, cause at least one device to perform operations including receiving a user query in response to a user query request. The user query is received at a first user interface. The device further performs operations including a step of determining one or more search terms from the user query using a query parser. The device further performs operations including a step of determining one or more semantically similar queries based on the one or more search terms of the user query. The device further performs operations including a step of searching for information related to the one or more search terms from one or more databases. The search uses one or more machine learning models. The device further performs operations including a step of generating an output to the user query. The output is generated based on the information related to the one or more search terms. The output includes at least a portion of the information related to the one or more search terms. The output further includes one or more citations associated with the information related to the one or more search terms from the one or more databases. The device further performs operations including a step of displaying the output to the user query at the first user interface.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

This description of the exemplary embodiments is intended to be read in connection with the accompanying drawings, which are to be considered part of the entire written description. Terms concerning data connections, coupling and the like, such as "connected" and "interconnected," and/or "in signal communication with" refer to a relationship wherein systems or elements are electrically connected (e.g., wired, wireless, etc.) to one another either directly or indirectly through intervening systems, unless expressly described otherwise. The term "operatively coupled" is such a coupling or connection that allows the pertinent structures to operate as intended by virtue of that relationship.

In the following, various embodiments are described with respect to the claimed systems as well as with respect to the claimed methods. Features, advantages, or alternative embodiments herein may be assigned to the other claimed objects and vice versa. In other words, claims for the systems may be improved with features described or claimed in the context of the methods. In this case, the functional features of the method are embodied by objective units of the systems. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

Furthermore, in the following, various embodiments are described with respect to methods and systems for machine-learning based content searching. Machine-learning based content searching includes receiving a user query in response to a user query request. From the user query, one or more search terms satisfying search term criteria may be selected. A search for information related to the one or more search terms may be performed at one or more databases. Based on the resulting information, an output to the user query may be generated and displayed to the user. In some embodiments, the output includes at least a portion, or a summary of, the information related to the one or more search terms from the one or more databases. The output may also include one or more citations associated with the information related to the one or more search terms from the one or more databases. For example, the methods and systems may include every citation associated with information used in the output.

Figure 1:
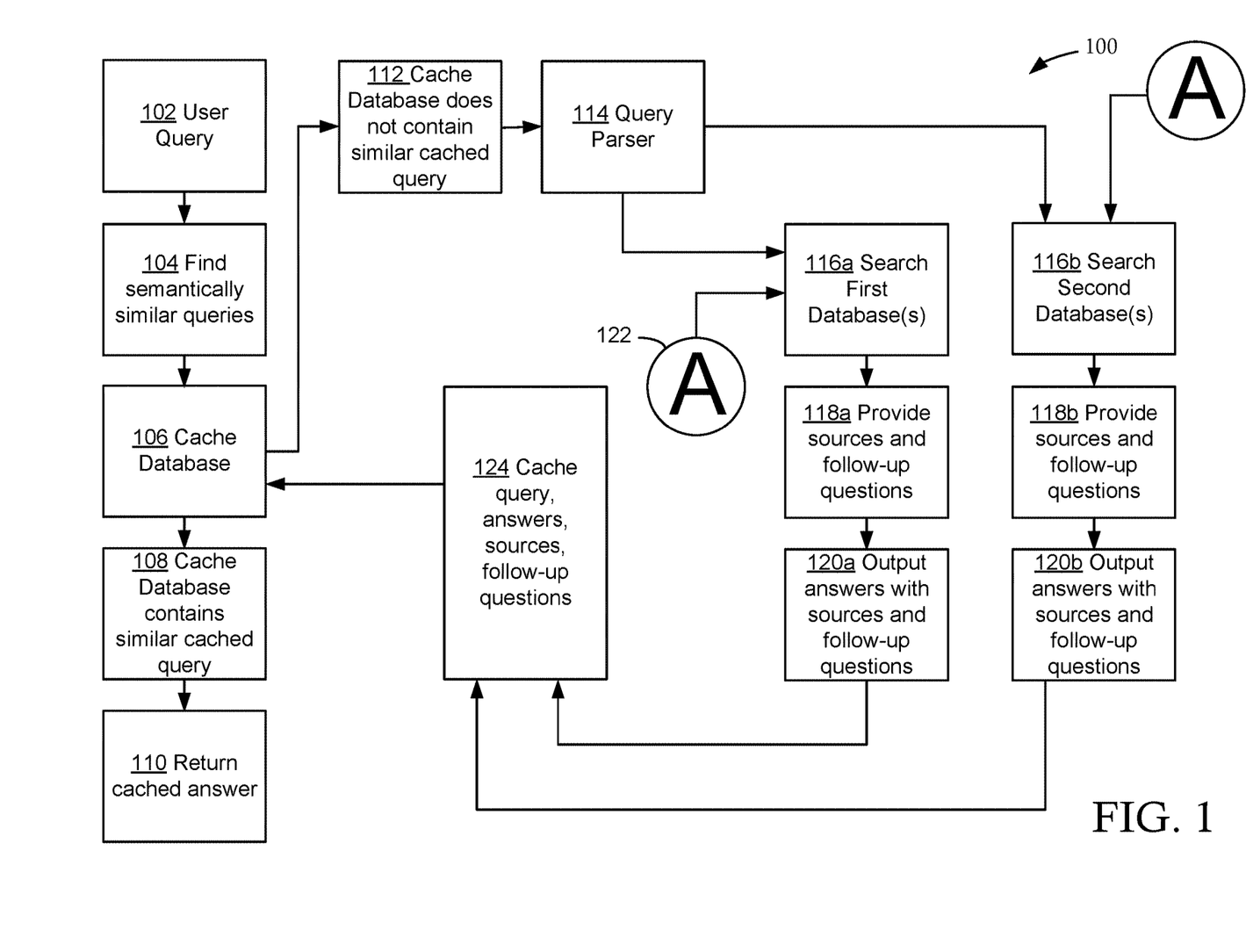
FIG. 1 is a block diagram illustrating various portions of a system configured to search one or more databases using one or more machine learning models, in accordance with some embodiments.

FIG. 1 is a block diagram 100 illustrating various portions of a system configured to search one or more databases using one or more machine learning models, in accordance with some embodiments. A user query 102 may be in the form of natural language. For example, the user query may be in a conversational tone. In this example, the user query is posed as a question the user would ask a doctor. In some embodiments, the user query is not limited to a particular formatting (e.g., structured searching, exact match searching, or literal searching) or word choice. Generally, the user query request may be in any form, such as a search box implemented on a user interface.

A search system configured to receive a user query 102 in the form of natural language may reduce an amount of knowledge of the search system required when compared to conventional search solutions. For example, conventional search systems require a prerequisite understanding of the expected search format. Specifically, when multiple search terms are included in a user query, conventional search systems require the use of Boolean connectors to direct those conventional search systems how to parse, or interpret, the user query. In this example, without the prerequisite understanding of the Boolean connectors, a user may input a query with the intention that only one of the terms is required (e.g., an "OR" connecting operator), while the default mode of search for the conventional search system searches all the terms (e.g., an "AND" connecting operator). The mismatch between intention of the user and operation of the user may lead to incorrect search results and/or a frustrating user experience. A natural language search may not require the same level of rigidity. The natural language search may determine the intended meaning of the user query and adapt the search based on the intended meaning. Stated more succinctly, conventional search systems require strict syntax rules whereas natural language searching is capable of understanding and interpreting the meaning of the user query and may search accordingly. As a result, natural language searching may allow users to input a user query that is more conversational in tone without reducing the accuracy and relevancy of the search results. Furthermore, natural language searching may capture a broader range of relevant search results.

Another advantage of a search system configured to receive a user query 102 in the form of natural language may include a reduced required knowledge of the search domain when compared to conventional search solutions. For example, using natural language may allow a user to describe a domain-specific query, such as a medical issue, without specific domain knowledge, such as specific knowledge regarding the medical issue. In this example, the user may describe his or her demographics information and the symptoms experienced without a preliminary diagnosis to guide the search system. In contrast, conventional search systems require certain search terms and/or language to provide relevant materials.

In some embodiments, the user query 102 may include one or more specific terms to improve the accuracy of the output associated with the user query 102. As used herein, "specific terms" may refer to domain-specific slots that are expected to have a value within the context of the domain (e.g., such as a search within a medical domain expecting one or more of a diagnosis, procedure, medication, etc.). The search system may be operable without any or all of the one or more specific terms. For example, the search system may perform a search with a natural language user query without the specified terms. In this example, the search system will determine likely candidates related to the one or more specific terms based on the natural language user query. In some embodiments, the search system may require at least one of the specific terms. For example, the search system for searching for drug related information may require at least one term in the user query to be a brand name of a drug, a generic name of the drug, an active ingredient of the drug, or other identifying information regarding the drug. In some embodiments, the user is prompted to add specific terms to the user query. The user may be prompted when the user query is too vague or results in too much information. For example, a user query of "nauseas man" may result in the search system prompting the user for more information. In this example, the question may result in too many potential answers and the search system may request a new user query or may request additional information regarding at least one of the specified terms. Additionally, the aforementioned example user query 102 may lack a required specified term. An example required specified term may include a name and/or other identifier of a drug or class of drugs.

The one or more specific terms may include a drug name, a health indication (e.g., medical condition), a specific population, etc. A health indication may include vital signs (e.g., heart rate, blood pressure, and/or body temperature), physical symptoms (e.g., pain, fatigue, nausea, rashes, swelling, and/or discoloration), and/or mental health symptoms. A specific population may include adults, adult male, adult female, pregnant, senior, child, pregnancy, lactation, females of reproductive potential, males of reproductive potential, pediatric, geriatric, renal impairment, hepatic impairment, etc. A specific population term may be unknown. For example, when the specific population term is unknown, the search system may search for information without respect to specific populations and/or searches across all specific populations.

The one or more specific terms may also include drug related terms such as a dosing (e.g., a drug dosing), a usage, a contraindication, a warning, a reaction, an interaction, clinical studies, a precaution, a strength. Dosing may include an amount and/or frequency of the drug to be administered, where to administer the drug, how to administer the drug, etc. Usage may include information related to the purpose and/or limitations of the drug. A contraindication may include information related to contraindications of the drug (e.g., conditions that make the drug potentially harmful to the individual). A reaction may include information related to adverse reactions or side effects related to the drug and/or information related to adverse reactions or side effects for a particular dosing of the drug and/or a specific population (e.g., male and/or female). An interaction may include information relating to interactions of the drug in question with other drugs, clinical studies may include information relating to clinical studies of the drug, a precaution may include information related to safety, precautions, and monitoring steps to be taken for the drug, and a strength may include information related to the form and/or the strength of the drug.

In some embodiments, one or more semantically similar queries 104 are determined based on the user query 102. The semantically similar queries 104 may include generated queries having similar meaning or semantic content as the user query 102. For example, a generated query may substitute one or more terms for one or more other terms in a query (e.g., substituting a first value of a specific term for a second, equivalent value of the specific term, such as substituting a generic drug name for a brand name, a second brand name for a first brand name, etc.). The one or more semantically similar queries 104 may be determined based on meeting similarity criteria. In some embodiments, the similarity criteria is based on a query-level comparison (e.g., an entire semantically similar query is compared to an entire user query). The similarity criteria may be based on a number of matching terms between the user query and each of the one or more semantically similar queries 104 satisfying a threshold number. Matching terms can include direct matches or semantically similar matches. An example of a direct match may include "ASPIRIN" included in both the semantically similar query 104 and the user query 102. An example of a semantically similar match may include "acetaminophen" included in the semantically similar query 104 and "TYLENOL" included in the user query 102. These terms may be considered semantically similar because TYLENOL is a brand name for acetaminophen. The threshold number may include a specified minimum number, and/or based on a percentage of the semantically similar query 104 matching the user query 102. Certain terms may be required to be matching for the user query and the semantically similar query to be semantically similar. For example, in some embodiments, the same or similar drug term must be included in both the user query and the semantically similar query for the two queries to be semantically similar. The similarity criteria may be based on comparing the entire semantically similar query to the entire user query without a term-by-term comparison. The similarity criteria may be based on a term-by-term comparison between the user query and the one or more semantically similar queries 104. For example, each term of the user query may be compared to a matching term, if present, in the one or more semantically similar queries.

In some embodiments, the one or more semantically similar queries may be identified by one or more semantic-similarity machine learning models configured to identify and/or determine semantic similarity between a user query 102 and one or more other queries, such as one or more historical queries, one or more generated queries, etc. The one or more semantic-similarity machine learning models may be the same as or distinct from one or more machine learning models for searching and/or one or more query parsing machine learning models, both discussed below.

In some embodiments, one or more semantically similar queries 104 are generated based on the user query 102. The generation of the one or more semantically similar queries 104 may be performed by one or more trained machine learning models (e.g., a trained large language model). The generated one or more semantically similar queries 104 may be used to search a cache database 106 for one or more stored user queries (e.g., past user queries). Searching the cache database 106 with semantically similar queries 104 in addition to the user query 102 may increase the number of relevant results. Generating the semantically similar queries 104 may be based on a similarity threshold and/or a distance between the generated semantically similar queries and the user query. In one example, the distance may be based on comparing an embedding of the generated semantically similar query to the user query 102. In another example, a lower similarity threshold may increase the number of semantically similar queries 104, and a higher similarity threshold may limit the number of semantically similar queries 104. More semantically similar queries 104 may be advantageous when the user query 102 is a query regarding an overview or otherwise high-level search of a topic. Less semantically similar queries 104 may be advantageous when the user query is specific in nature. For example, a specific user query may include a query regarding a single brand name drug for a specific population with regards to dosing. In this example, a lower similarity threshold may be selected to match the user's intention for a tailored search.

The semantically similar queries 104 may be used in conjunction with the user query 102 to provide a more comprehensive search. For example, the inclusion of semantically similar queries 104 may broaden the search and potentially capture information that is of interest to the user, but was not covered in the user query 102. The user query 102 and/or the one or more semantically similar queries 104 may be compared to one or more stored queries in a cache database 106. The one or more stored queries may include historical and/or past user queries. The stored queries may include commonly searched user queries. For example, stored queries may include user queries regarding the common cold. User queries may be stored as stored queries based on a threshold number of searches for that query and/or related user queries or based on a specified number of top user queries. The cache database 106 may include one or more stored user queries, one or more stored information associated with a respective stored user query, one or more stored citations associated with the information, and/or one or more follow up queries associated with the stored query. The cache database 106 may advantageously increase the processing speed and reduce the bottleneck for accessing data in response to a user query 102. For example, accessing a cache database 106 may be more efficient than accessing a third-party database. Another advantage may be caching user queries 102 and results for commonly searched queries (e.g., questions) and information.

When the cache database 106 contains 108 a stored (e.g., cached) user query similar to the user query 102, the search system may return 110 the stored (e.g., cached) output and/or stored information associated with the stored user query. When the cache database does not contain 112 a stored (e.g., cached) user query similar to the user query 102, the search system may pass the user query to the query parser 114. In some embodiments, the query parser 114 determines one or more search terms from the user query 102. The one or more search terms may be determined from the terms present in a user query in the form of a natural language. For example, the one or more search terms may include the one or more specific terms identified in the original query (e.g., one or more medical terms). The one or more specific terms may include a drug name, a health indication, a specific population, etc. The search terms may be identified using any suitable term identification process, such as a semantic process, a slot filling process, etc.

In some embodiments, the query parser 114 determines a type of query corresponding to the user query 102. As used herein, the term "type" refers to a categorical definition of the query within a given domain. For example, within the context of a medical domain, the query parser 114 may determine that the user query 102 corresponds to one or more of dosing, usage, contraindication, warning, adverse reaction, drug interactions, clinical studies, precaution, specific population, dosage forms and strengths, etc. In this example, the user query 102 corresponds to a question regarding the dosing of acetaminophen. In another example, the query parser 114 determines that the user query 102 is directed to an adverse reaction question. Additional query types may be based on the one or more specific terms and/or domain-specific categories.

In some embodiments, the query parser 114 limits a search boundary of the search system. For example, the query parser 114 may limit a search boundary of a machine learning model of the search system. In another example, the query parser 114 may limit the search to a particular type of query (e.g., dosing related query or adverse reaction query) the machine learning model can choose.

In some embodiments, the search terms are passed to a machine learning model and/or a large language model to search one or more databases. For example, a user query 102 may include five terms and the query parser 114 may identify three of the terms as search terms based on a search term criteria. Search term criteria may include, but is not limited to, matching one or more specific term slots within a corresponding domain, matching a list of expected search terms, being semantically similar to one or more prior search terms, etc. The three search terms may be passed to a trained machine learning model and/or a trained large language model. In this example, the trained machine learning model and/or a trained large language model may search one or more databases for information related to, and/or regarding, the three search terms that were passed by the query parser 114. The remaining two terms of the user query 102 are not passed on to the model. For example, the non-search terms may include generic terms that would result in broad search results and/or terms that are not a specific term expected within the domain, e.g., articles (e.g., "a," "the," "me," etc.), non-domain terms (e.g., a term referencing "power" within a medical domain, etc. As such, the remaining two terms may not used in the search. In some embodiments, all of the terms are provided to a searching model but the search terms are given a larger weight than the other terms of the user query 102.

In some embodiments, an error message is generated when a search is outside the scope of a corresponding searching system. The error may be displayed to the user via the first user interface. The error may request a different user query from the user. For example, an error may be generated when none of the one or more search terms satisfy a search term criteria or when the user query includes one or more terms, but the terms are outside the knowledge domain of the search system. When the query parser 114 receives an invalid query, the query parser 114 may request a user query with one or more terms within a predetermined knowledge domain, such as one or more terms in a medical domain. For example, a query regarding automotive maintenance may result in an error for a search system configured to answer questions regarding medical issues. As another example, an error may be generated when a type of question associated with the user query 102 is invalid. An invalid type of question may include "How are you?"

In some embodiments, a query may be invalid for not including each required search term within a domain. For example, within a medical domain, a search system may output an error when a user query 102 only includes a symptom, without additional search terms such as demographics, drug information, diagnosis, etc., as the search system may have insufficient information to perform a search of the one or more databases. An invalid query may also include prohibited search terms, such as concepts related to harming another or self-harm.

In some embodiments, the query parser 114 includes a machine learning model for parsing the user query 102. The machine learning model for parsing the user query 102 may be distinct from the one or more machine learning models for searching and/or may be the same as, or integrated with, other machine learning models described herein. A machine learning model for parsing the user query 102 may include a large language model and/or one or more generative pre-trained transformers.

In some embodiments, the query parser 114 includes a spell check and correction component. For example, if the user spells the drug name incorrectly, the query parser 114 may correct the spelling of the drug before sending it to a machine learning model (e.g., a large language model). In another example, if the user spells an indication incorrectly, or uses layman terms instead of medical terms, the query parser 114 may correct the spelling of the indication or substitute the layman terms with the appropriate medical terms.

In some embodiments, the query parser 114 selects at least one of one or more machine learning model and at least one of one or more databases for a search. For example, the query parser 114 may select to search PubMed only, DailyMed only, or both PubMed and DailyMed. In this example, the query parser 114 may also select a respective machine learning model associated with searching the selected database(s). The selection of at least one machine learning model and/or at least one database may be based on the one or more search terms, such as the one or more search terms matching specified search routing criteria. The specified search routing criteria may be based on the information included within the one or more databases. For example, a user query 102 containing a term related to drug A may be routed to database A with machine learning model A for searching database A, and a different user query 102 containing a term related to drug B may be routed to database B with machine learning model B for searching database B.

In some embodiments, the query parser 114 passes the one or more search terms to a first machine learning model for searching a first database 116a, a second machine learning model for searching second database 116b, and/or both databases 116a, 116b. A machine learning model may be configured to search a single, respective database, search more than one database, search available databases, and/or search for information related to the one or more search terms of the user query 102 from a respective database. In some embodiments, the search is in accordance with a determination that the user query 102 and the one or more semantically similar queries have not been previously searched and/or is not stored in a cache database. A machine learning model may be configured to search for information from a cache database 122 based on a respective database (e.g., third party database) prior to and/or in conjunction with searching the corresponding database.

In some embodiments, a machine learning model includes a hybrid retrieval model. The hybrid retrieval may include one or more filters. The one or more filters may be based on the one or more search terms. For example, the one or more filters may include a drug name filter, where only documents, and/or other sources, that include the drug name (as provided in the user query 102) may be searched based on the one or more search terms of the user query 102. In this example, the one or more filters may perform filtration before the search for information. In another example, the one or more filters may limit the output to relevant sections of the document. In this example, the one or more filters may perform filtration after the search for information. A hybrid retrieval process may include finding n-most relevant snippets of text to inject into the prompt. For example, a hybrid retrieval model may add additional search terms to be search based on the search terms from the user query. The additional search terms may broaden the search and the resulting information. Furthermore, the additional search terms may result in a more accurate and/or more focused search. A hybrid retrieval model may additionally or alternatively include injecting predetermined terms, such as brand names, into the search terms of the user query 102. For example, a hybrid retrieval model may modify a user query 102 to include similar drug brand names to a searched drug. The similar drug brand names may include both brand name drugs and generic versions of the brand name drugs. The additional drug names may be based on the health indication and/or active ingredient of the drug in the one or more search terms of the user query 102.

In some embodiments, an output 120a, 120b is generated for the user query based 102 on the information related to the one or more search terms of the user query 102. The output includes at least a portion of, or a summary of, information related to the one or more search terms. For example, an output may include a relevant snippet from a document, a summary of multiple relevant documents, etc. The output may include one or more citations 118a, 118b associated with the information related to the one or more search terms from the one or more databases. The one or more citations may include the source document for the information, such as, for example, an exact location within the source for the information. The one or more citations may include links to the source document.

In some embodiments, an output includes one or more follow-up questions. The one or more follow-up questions may include questions and/or queries that are relevant to the information provided in the output. The one or more follow-up questions may also include semantically similar queries. In some embodiments, an output 120a, 120b may be displayed on and/or integrated into a generated user interface, such as a first user interface. The first user interface for displaying the output 120a, 120b may be the same interface that the user used to enter the user query.

In some embodiments, the user query 102 and the output 120a, 120b may be stored in a cache database 124. One or more components of the output 120a, 120b, such as the information, one or more citations 118a, 118b, and/or one or more follow-up questions may be stored together (e.g., stored with reference and/or linking between the respective items).

Figure 2:
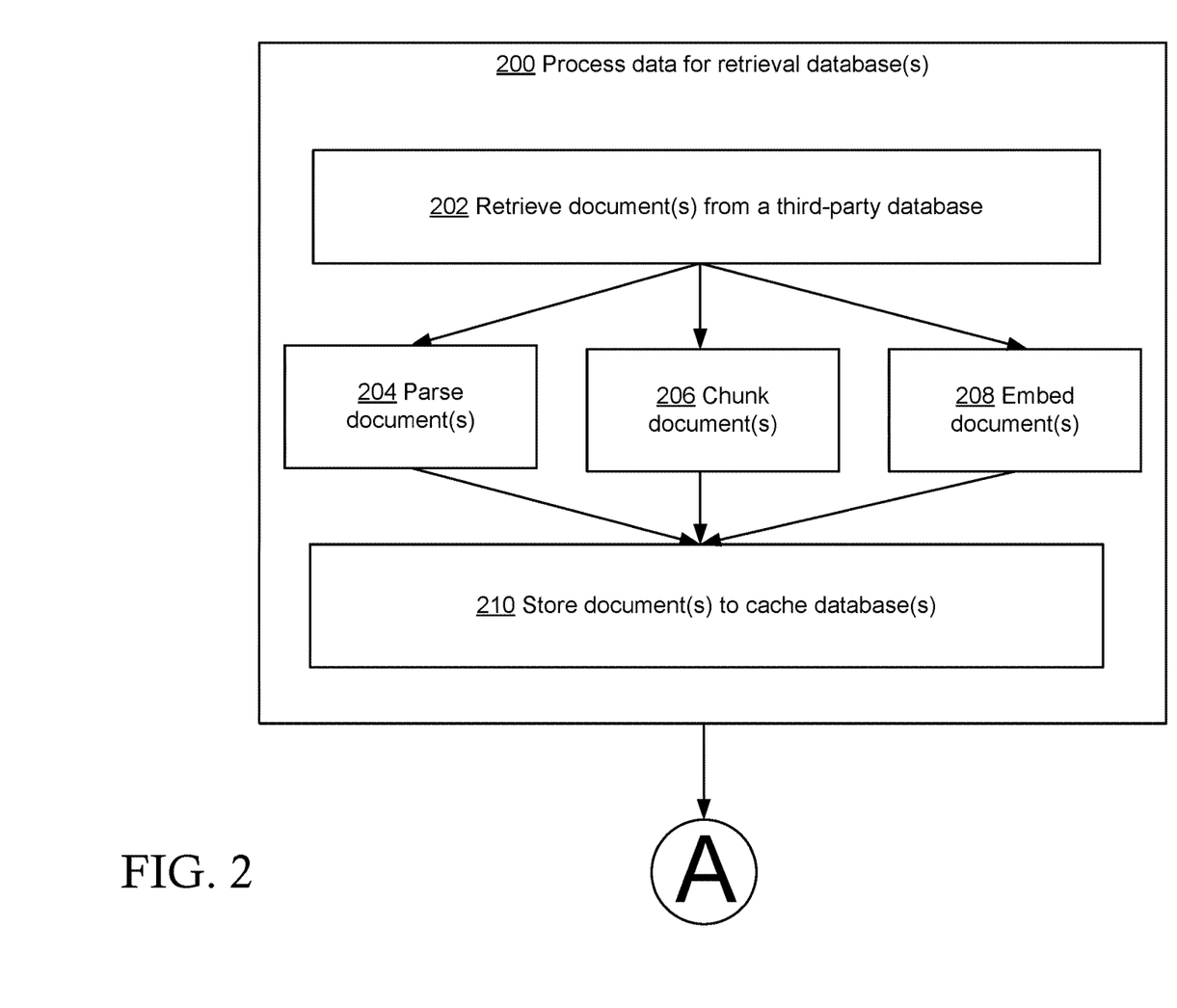
FIG. 2 is a block diagram illustrating various portions of a system configured to process of one or more document from one or more retrieval databases to be stored in one or more storage databases, in accordance with some embodiments.

FIG. 2 is a block diagram illustrating various portions of a system configured to process of one or more documents from one or more retrieval databases to be stored in one or more storage databases, in accordance with some embodiments. In some embodiments, a cache database is configured to process 200 one or more documents from the one or more databases (e.g., third-party databases). One or more documents may be retrieved 202 from one or more databases. The one or more documents may be parsed 204, chunked 206, embedded 208, and/or stored 210 in the one or more cache databases. The cache databases may be a cloud-based database and/or a local database. Storing 210 the processed documents in the cache database may be advantageous as the processed documents may be more quickly accessed when in comparison to the documents in a third-party database. Another advantage may be that an outage or otherwise unavailability of the third-party database will not impact the usability of the search system.

Figure 3:
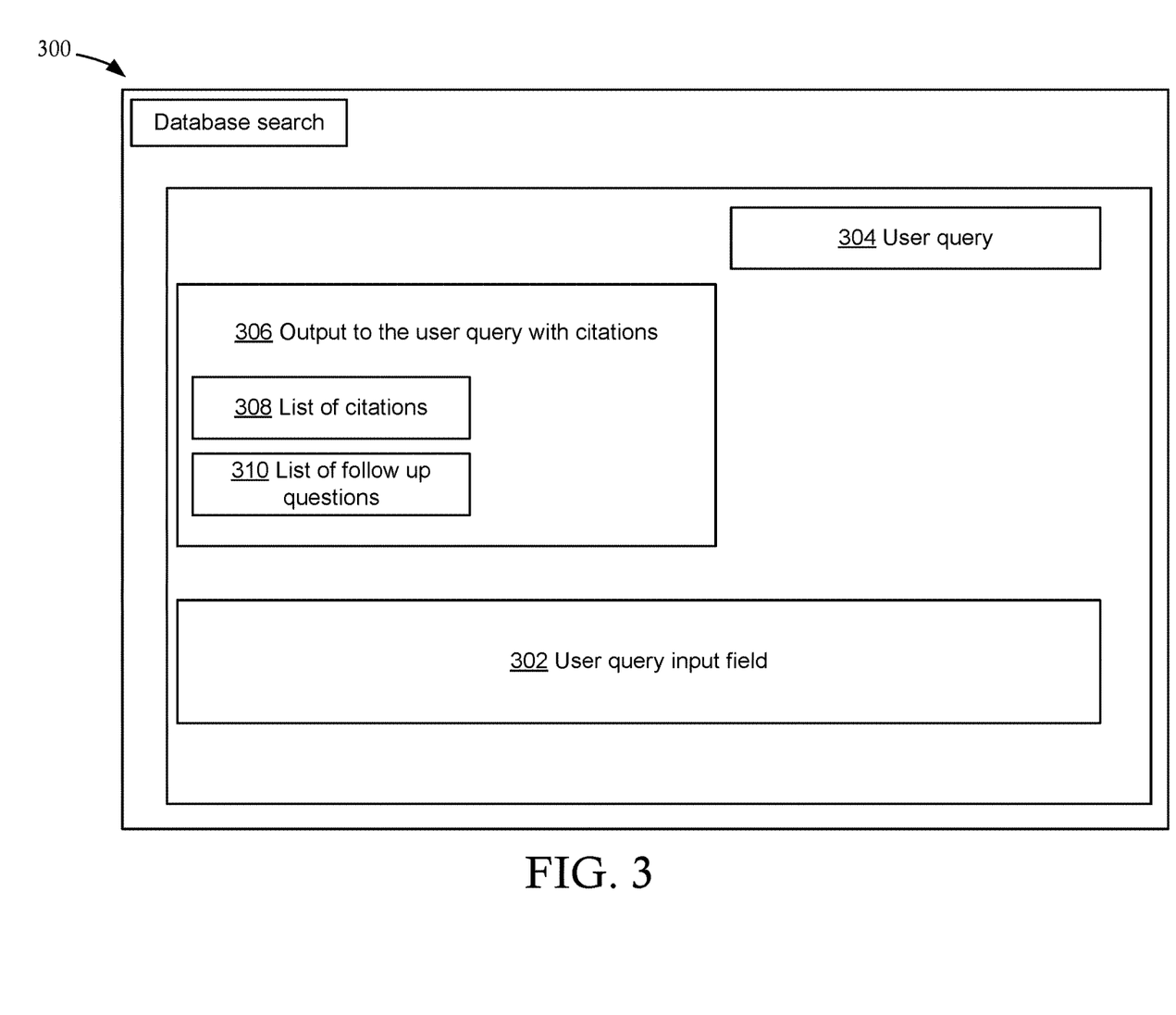
FIG. 3 is an example user interface for one or more user queries and output to the one or more user queries, in accordance with some embodiments.

FIG. 3 is an example user interface 300 for one or more user queries and output to the one or more user queries, in accordance with some embodiments. In some embodiments, the user interface 300 includes a user query input field 302. When a user query is inputted via the user query input field 302, or when the search system has a previous user query, the user query is displayed as user query 304. An output, e.g., result, for the user query 304, may be display as output 306. The output 306 may include citations 308 and/or follow up questions 310. The citations 308 may include one or more references to one or more sources (e.g, a document and/or other file) from the one or more databases, where the source includes information related to the user query 304. The list of citations 308 may be expandable. For example, until the user interacts with a citation element, the citations may remain collapsed to reduce the amount of screen space used. In response to a first interaction, the list of citations may be expanded to show the one or more citations 308. The one or more citations may include reference links to the source document. For example, clicking on citation A may open a new tab with the associated source document A. Selecting a follow-up question 310 may auto-populate the user query input field 302 and may automatically submit the selected follow-up question as a user query 304.

Figure 4:
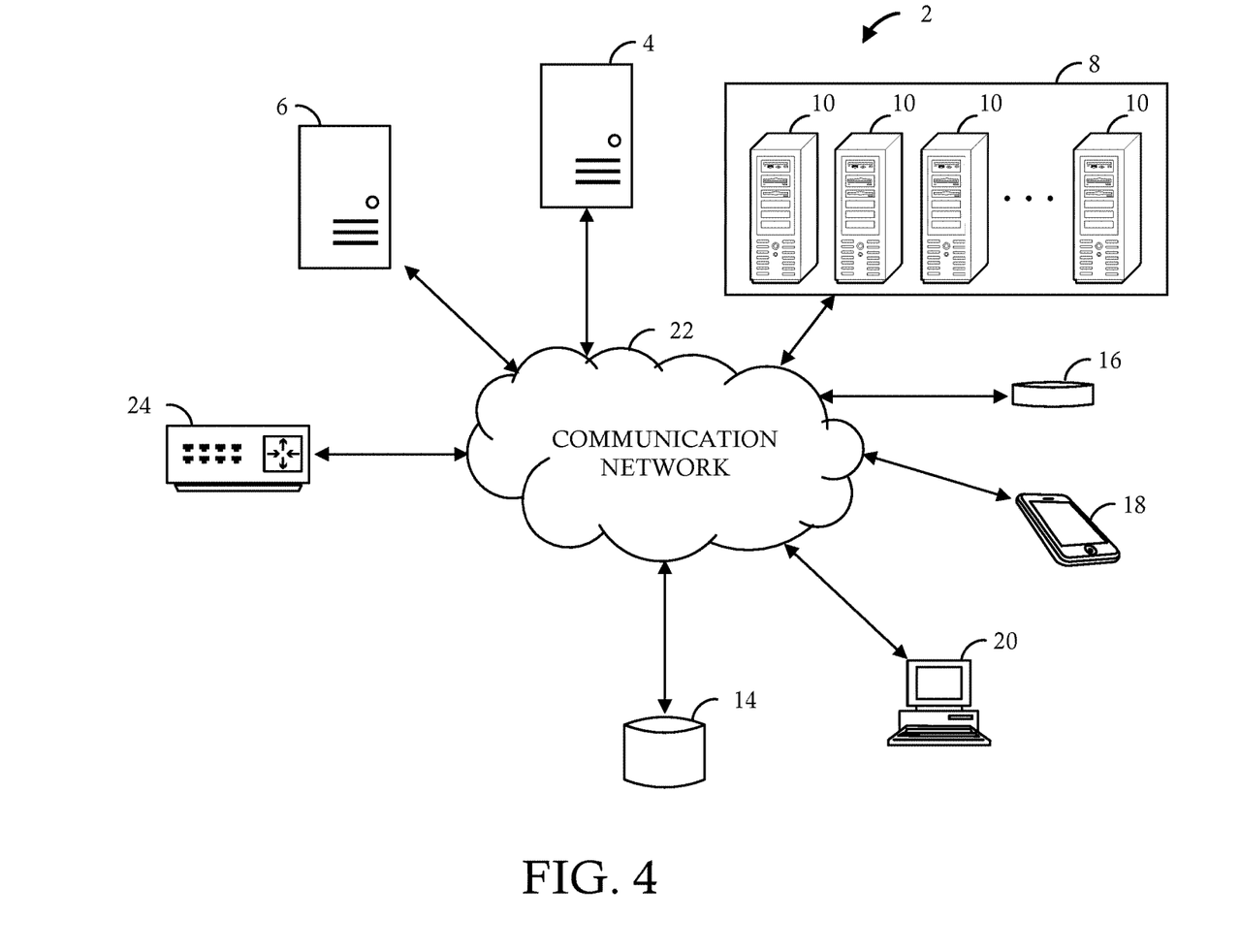
FIG. 4 illustrates a network environment configured to perform database searching using one or more machine learning models, in accordance with some embodiments.

FIG. 4 illustrates a network environment 2 configured to perform database searching using one or more machine learning models, in accordance with some embodiments. The network environment 2 includes a plurality of devices or systems configured to communicate over one or more network channels, illustrated as a network cloud 22. For example, in various embodiments, the network environment 2 may include, but is not limited to, search system device 4, a web server 6, a cloud-based engine 8 including one or more processing devices 10, a database 14, and/or one or more user computing devices 16, 18, 20 operatively coupled over the network 22. The search system device 4, the web server 6, the processing device(s) 10, and/or the user computing devices 16, 18, 20 may each be a suitable computing device that includes any hardware or hardware and software combination for processing and handling information. For example, each computing device may include, but is not limited to, one or more processors, one or more field-programmable gate arrays (FPGAs), one or more application-specific integrated circuits (ASICs), one or more state machines, digital circuitry, and/or any other suitable circuitry. In addition, each computing device may transmit and receive data over the communication network 22.

In some embodiments, each of the search system device 4 and the processing device(s) 10 may be a computer, a workstation, a laptop, a server such as a cloud-based server, or any other suitable device. In some embodiments, each of the processing devices 10 is a server that includes one or more processing units, such as one or more graphical processing units (GPUs), one or more central processing units (CPUs), and/or one or more processing cores. Each processing device 10 may, in some embodiments, execute one or more virtual machines. In some embodiments, processing resources (e.g., capabilities) of the one or more processing devices 10 are offered as a cloud-based service (e.g., cloud computing). For example, the cloud-based engine 8 may offer computing and storage resources of the one or more processing devices 10 to the search system device 4.

In some embodiments, each of the user computing devices 16, 18, 20 may be a cellular phone, a smart phone, a tablet, a personal assistant device, a voice assistant device, a digital assistant, a laptop, a computer, or any other suitable device. In some embodiments, the web server 6 hosts one or more network environments, such as an e-commerce network environment. In some embodiments, the search system device 4, the processing devices 10, and/or the web server 6 are operated by the network environment provider, and the user computing devices 16, 18, 20 are operated by users of the network environment. In some embodiments, the processing devices 10 are operated by a third party (e.g., a cloud-computing provider).

Although FIG. 4 illustrates three user computing devices 16, 18, 20, the network environment 2 may include any number of user computing devices 16, 18, 20. Similarly, the network environment 2 may include any number of the plan personalization computing device 4, the web server 6, the processing devices 10, and/or the databases 14. It will further be appreciated that additional systems, servers, storage mechanism, etc. may be included within the network environment 2. In addition, although embodiments are illustrated herein having individual, discrete systems, it will be appreciated that, in some embodiments, one or more systems may be combined into a single logical and/or physical system. For example, in various embodiments, one or more of the search system device 4, the web server 6, the database 14, the user computing devices 16, 18, 20, and/or the router 24 may be combined into a single logical and/or physical system. Similarly, although embodiments are illustrated having a single instance of each device or system, it will be appreciated that additional instances of a device may be implemented within the network environment 2. In some embodiments, two or more systems may be operated on shared hardware in which each system operates as a separate, discrete system utilizing the shared hardware, for example, according to one or more virtualization schemes.

The communication network 22 may be a WiFi® network, a cellular network such as a 3GPP® network, a Bluetooth® network, a satellite network, a wireless local area network (LAN), a network utilizing radio-frequency (RF) communication protocols, a Near Field Communication (NFC) network, a wireless Metropolitan Area Network (MAN) connecting multiple wireless LANs, a wide area network (WAN), or any other suitable network. The communication network 22 may provide access to, for example, the Internet.

Each of the user computing devices 16, 18, 20 may communicate with the web server 6 over the communication network 22. For example, each of the user computing devices 16, 18, 20 may be operable to view, access, and interact with a website, such as a knowledge-based website, hosted by the web server 6. The web server 6 may transmit user session data related to a user's activity (e.g., interactions) on the website. For example, a user may operate one of the user computing devices 16, 18, 20 to initiate a web browser that is directed to the website hosted by the web server 6. The user may, via the web browser, perform various operations such as obtaining predetermined interface and/or content elements determined by one or more preselected content plans, interacting with one or more assessment and/or input interface elements, obtaining customized interface elements, content elements, and/or assessment elements determined by one or more personalized interface content plans, etc. The website may capture these activities as user session data, and transmit the user session data to the search system device 4 over the communication network 22. The website may also allow the user to interact with one or more of interface elements to perform specific operations, such as selecting one or more elements for further processing. In some embodiments, the web server 6 transmits user interaction data identifying interactions between the user and the website to the search system device 4.

In some embodiments, the search system device 4 may execute one or more models, processes, or algorithms, such as a machine learning model, deep learning model, statistical model, etc., to search one or more databases based on a user query. The search system device 4 may transmit an output associated with the user query, including at least a portion of the information related to the one or more search terms and one or more citations associated with the information related to the one or more search terms from the one or more databases, to the web server 6 over the communication network 22, and the web server 6 may display interface elements associated with the output to the user query on the website to the user. For example, the web server 6 may display interface elements associated with the search system and the output to the user query to the user on a search-based interface configured to convey information to the user and/or to prompt the user to enter another user query.

The search system device 4 is further operable to communicate with the database 14 over the communication network 22. For example, the search system device 4 may store data to, and read data from, the database 14. The database 14 may be a remote storage device, such as a cloud-based server, a disk (e.g., a hard disk), a memory device on another application server, a networked computer, or any other suitable remote storage. Although shown remote to the plan personalization computing device 4, in some embodiments, the database 14 may be a local storage device, such as a hard drive, a non-volatile memory, or a USB stick. The search system device 4 may store interaction data received from the web server 6 in the database 14. The search system device 4 may also receive from the web server 6 user session data identifying events associated with browsing sessions, and may store the user session data in the database 14.

In some embodiments, the search system device 4 generates training data for a plurality of models (e.g., machine learning models, deep learning models, statistical models, algorithms, etc.) based on aggregation data, historical user session data, search data, assessment data, interaction data, etc. The search system device 4 and/or one or more of the processing devices 10 may train one or more models based on corresponding training data. The search system device 4 may store the models in a database, such as in the database 14 (e.g., a cloud storage database).

The models, when executed by the search system device 4, allow the search system device 4 to parse a user query for one or more search terms, search one or more databases for information regarding the one or more search terms, and output the information with citations to a user. For example, the search system device 4 may obtain one or more models from the database 14. The search system device 4 may then receive, in real-time from the web server 6, a request for information associated with a user query. In response to receiving the request to for information associated with the user query, the search system device 4 may execute one or more models to parse the user query into one or more search terms, and search one or more databases for information regarding the one or more search terms.

In some embodiments, the search system device 4 assigns the models (or parts thereof) for execution to one or more processing devices 10. For example, each model may be assigned to a virtual machine hosted by a processing device 10. The virtual machine may cause the models or parts thereof to execute on one or more processing units such as GPUs. In some embodiments, the virtual machines assign each model (or part thereof) among a plurality of processing units. Based on the output of the models, search system device 4 may generate a personalized interface content plan.

Figure 5:
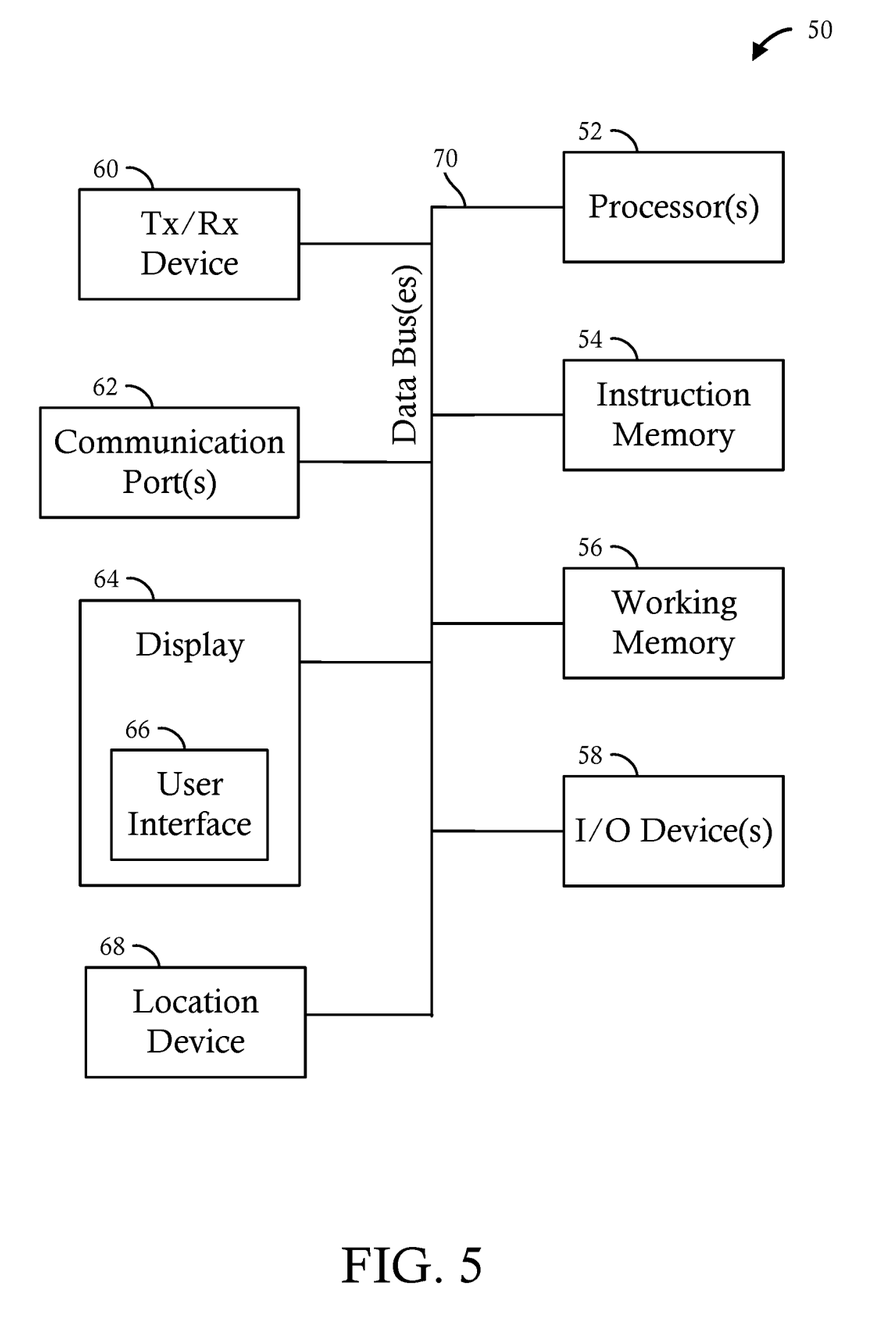
FIG. 5 illustrates block diagram of a computer device configured to implement one or more processes, in accordance with some embodiments.

FIG. 5 illustrates a block diagram of a computing device 50 configured to implement one or more processes, in accordance with some embodiments. In some embodiments, each of the search system device 4, the web server 6, the one or more processing devices 10, the workstation(s) 12, and/or the user computing devices 16, 18, 20 in FIG. 4 may include the features shown in FIG. 5. Although FIG. 5 is described with respect to certain components shown therein, it will be appreciated that the elements of the computing device 50 may be combined, omitted, and/or replicated. In addition, it will be appreciated that additional elements other than those illustrated in FIG. 5 may be added to the computing device.

As shown in FIG. 5, the computing device 50 may include one or more processors 52, an instruction memory 54, a working memory 56, one or more input/output devices 58, a transceiver 60, one or more communication ports 62, a display 64 with a user interface 66, and an optional location device 68, all operatively coupled to one or more data buses 70. The data buses 70 allow for communication among the various components. The data buses 70 may include wired, or wireless, communication channels.

The one or more processors 52 may include any processing circuitry operable to control operations of the computing device 50. In some embodiments, the one or more processors 52 include one or more distinct processors, each having one or more cores (e.g., processing circuits). Each of the distinct processors may have the same or different structure. The one or more processors 52 may include one or more central processing units (CPUs), one or more graphics processing units (GPUs), application specific integrated circuits (ASICs), digital signal processors (DSPs), a chip multiprocessor (CMP), a network processor, an input/output (I/O) processor, a media access control (MAC) processor, a radio baseband processor, a co-processor, a microprocessor such as a complex instruction set computer (CISC) microprocessor, a reduced instruction set computing (RISC) microprocessor, and/or a very long instruction word (VLIW) microprocessor, or other processing device. The one or more processors 52 may also be implemented by a controller, a microcontroller, an application specific integrated circuit (ASIC), a field programmable gate array (FPGA), a programmable logic device (PLD), etc.

In some embodiments, the one or more processors 52 are configured to implement an operating system (OS) and/or various applications. Examples of an OS include, for example, operating systems generally known under various trade names such as Apple macOS™, Microsoft Windows™, Android™, Linux™, and/or any other proprietary or open-source OS. Examples of applications include, for example, network applications, local applications, data input/output applications, user interaction applications, etc.

The instruction memory 54 may store instructions that are accessed (e.g., read) and executed by at least one of the one or more processors 52. For example, the instruction memory 54 may be a non-transitory, computer-readable storage medium such as a read-only memory (ROM), an electrically erasable programmable read-only memory (EEPROM), flash memory (e.g. NOR and/or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, a removable disk, CD-ROM, any non-volatile memory, or any other suitable memory. The one or more processors 52 may be configured to perform a certain function or operation by executing code, stored on the instruction memory 54, embodying the function or operation. For example, the one or more processors 52 may be configured to execute code stored in the instruction memory 54 to perform one or more of any function, method, or operation disclosed herein.

Additionally, the one or more processors 52 may store data to, and read data from, the working memory 56. For example, the one or more processors 52 may store a working set of instructions to the working memory 56, such as instructions loaded from the instruction memory 54. The one or more processors 52 may also use the working memory 56 to store dynamic data created during one or more operations. The working memory 56 may include, for example, random access memory (RAM) such as a static random access memory (SRAM) or dynamic random access memory (DRAM), Double-Data-Rate DRAM (DDR-RAM), synchronous DRAM (SDRAM), an EEPROM, flash memory (e.g. NOR and/or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, a removable disk, CD-ROM, any non-volatile memory, or any other suitable memory. Although embodiments are illustrated herein including separate instruction memory 54 and working memory 56, it will be appreciated that the computing device 50 may include a single memory unit configured to operate as both instruction memory and working memory. Further, although embodiments are discussed herein including non-volatile memory, it will be appreciated that computing device 50 may include volatile memory components in addition to at least one non-volatile memory component.

In some embodiments, the instruction memory 54 and/or the working memory 56 includes an instruction set, in the form of a file for executing various methods, such as methods for generating personalized study plans, as described herein. The instruction set may be stored in any acceptable form of machine-readable instructions, including source code or various appropriate programming languages. Some examples of programming languages that may be used to store the instruction set include, but are not limited to: Java, JavaScript, C, C++, C#, Python, Objective-C, Visual Basic, .NET, HTML, CSS, SQL, NoSQL, Rust, Perl, etc. In some embodiments a compiler or interpreter is configured to convert the instruction set into machine executable code for execution by the one or more processors 52.

The input-output devices 58 may include any suitable device that allows for data input or output. For example, the input-output devices 58 may include one or more of a keyboard, a touchpad, a mouse, a stylus, a touchscreen, a physical button, a speaker, a microphone, a keypad, a click wheel, a motion sensor, a camera, and/or any other suitable input or output device.

The transceiver 60 and/or the communication port(s) 62 allow for communication with a network, such as the communication network 22 of FIG. 4. For example, if the communication network 22 of FIG. 4 is a cellular network, the transceiver 60 is configured to allow communications with the cellular network. In some embodiments, the transceiver 60 is selected based on the type of the communication network 22 the computing device 50 will be operating in. The one or more processors 52 are operable to receive data from, or send data to, a network, such as the communication network 22 of FIG. 4, via the transceiver 60.

The communication port(s) 62 may include any suitable hardware, software, and/or combination of hardware and software that is capable of coupling the computing device 50 to one or more networks and/or additional devices. The communication port(s) 62 may be arranged to operate with any suitable technique for controlling information signals using a desired set of communications protocols, services, or operating procedures. The communication port(s) 62 may include the appropriate physical connectors to connect with a corresponding communications medium, whether wired or wireless, for example, a serial port such as a universal asynchronous receiver/transmitter (UART) connection, a Universal Serial Bus (USB) connection, or any other suitable communication port or connection. In some embodiments, the communication port(s) 62 allows for the programming of executable instructions in the instruction memory 54. In some embodiments, the communication port(s) 62 allow for the transfer (e.g., uploading or downloading) of data, such as machine learning model training data.

In some embodiments, the communication port(s) 62 are configured to couple the computing device 50 to a network. The network may include local area networks (LAN) as well as wide area networks (WAN) including without limitation Internet, wired channels, wireless channels, communication devices including telephones, computers, wire, radio, optical and/or other electromagnetic channels, and combinations thereof, including other devices and/or components capable of/associated with communicating data. For example, the communication environments may include in-body communications, various devices, and various modes of communications such as wireless communications, wired communications, and combinations of the same.

In some embodiments, the transceiver 60 and/or the communication port(s) 62 are configured to utilize one or more communication protocols. Examples of wired protocols may include, but are not limited to, Universal Serial Bus (USB) communication, RS-232, RS-422, RS-423, RS-485 serial protocols, FireWire, Ethernet, Fibre Channel, MIDI, ATA, Serial ATA, PCI Express, T-1 (and variants), Industry Standard Architecture (ISA) parallel communication, Small Computer System Interface (SCSI) communication, or Peripheral Component Interconnect (PCI) communication, etc. Examples of wireless protocols may include, but are not limited to, the Institute of Electrical and Electronics Engineers (IEEE) 802.xx series of protocols, such as IEEE 802.11a/b/g/n/ac/ag/ax/be, IEEE 802.16, IEEE 802.20, GSM cellular radiotelephone system protocols with GPRS, CDMA cellular radiotelephone communication systems with 1×RTT, EDGE systems, EV-DO systems, EV-DV systems, HSDPA systems, Wi-Fi Legacy, Wi-Fi 1/2/3/4/5/6/6E, wireless personal area network (PAN) protocols, Bluetooth Specification versions 5.0, 6, 7, legacy Bluetooth protocols, passive or active radio-frequency identification (RFID) protocols, Ultra-Wide Band (UWB), Digital Office (DO), Digital Home, Trusted Platform Module (TPM), ZigBee, etc.

The display 64 may be any suitable display and may display the user interface 66. The user interfaces 66 may enable user interaction with the search system, information associated with a user query, citations for the output of the user query, and/or the information cited in the output. For example, the user interface 66 may be a user interface for an application of a network environment operator that allows a user to view and interact with the operator's website. In some embodiments, a user may interact with the user interface 66 by engaging the input-output devices 58. In some embodiments, the display 64 may be a touchscreen, where the user interface 66 is displayed on the touchscreen.

The display 64 may include a screen such as, for example, a Liquid Crystal Display (LCD) screen, a light-emitting diode (LED) screen, an organic LED (OLED) screen, a movable display, a projection, etc. In some embodiments, the display 64 may include a coder/decoder, also known as Codecs, to convert digital media data into analog signals. For example, the visual peripheral output device may include video Codecs, audio Codecs, or any other suitable type of Codec.

The optional location device 68 may be communicatively coupled to a location network and operable to receive position data from the location network. For example, in some embodiments, the location device 68 includes a GPS device configured to receive position data identifying a latitude and longitude from one or more satellites of a GPS constellation. As another example, in some embodiments, the location device 68 is a cellular device configured to receive location data from one or more localized cellular towers. Based on the position data, the computing device 50 may determine a local geographical area (e.g., town, city, state, etc.) of its position.

In some embodiments, the computing device 50 is configured to implement one or more modules or engines, each of which is constructed, programmed, configured, or otherwise adapted, to autonomously carry out a function or set of functions. A module/engine may include a component or arrangement of components implemented using hardware, such as by an application specific integrated circuit (ASIC) or field-programmable gate array (FPGA), for example, or as a combination of hardware and software, such as by a microprocessor system and a set of program instructions that adapt the module/engine to implement the particular functionality, which (while being executed) transform the microprocessor system into a special-purpose device. A module/engine may also be implemented as a combination of the two, with certain functions facilitated by hardware alone, and other functions facilitated by a combination of hardware and software. In certain implementations, at least a portion, and in some cases, all, of a module/engine may be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each module/engine may be realized in a variety of physically realizable configurations and should generally not be limited to any particular implementation exemplified herein, unless such limitations are expressly called out. In addition, a module/engine may itself be composed of more than one sub-modules or sub-engines, each of which may be regarded as a module/engine in its own right. Moreover, in the embodiments described herein, each of the various modules/engines corresponds to a defined autonomous functionality; however, in other contemplated embodiments, each functionality may be distributed to more than one module/engine. Likewise, in other contemplated embodiments, multiple defined functionalities may be implemented by a single module/engine that performs those multiple functions, possibly alongside other functions, or distributed differently among a set of modules/engines than specifically illustrated in the embodiments herein.

Searching databases may be burdensome and time consuming for user, especially when conventional search systems require a certain amount of prerequisite knowledge of the search domain and the search system. Conventional search systems for medical information require the user to have specific information related to the issue the user is searching about and format the search query to conform to what the conventional search system is expecting as an input. Thus, the user frequently has to perform multiple searches to find the correct terms and the correct formatting.

Systems including large language models, as disclosed herein, significantly reduce this problem, allowing for the search system to receive a natural language search query. For example, in some embodiments described herein, the search system can parse the natural language search query for one or more search terms, and search the one or more databases with the one or more search terms. Furthermore, the search system may determine and/or generate semantically similar user queries or semantically similar search terms to broaden the information that is outputted to the user. Additionally, the search system may summarize various sources of information. The search system may improve the speed of the user's search by requiring less searches and reducing the number of content the user has to read to obtain the information. The search system is additionally beneficial by providing citations to where the information was obtained and/or synthesized from. Citations allow the user to confirm the veracity of the information outputted by the search system.

Figure 6:
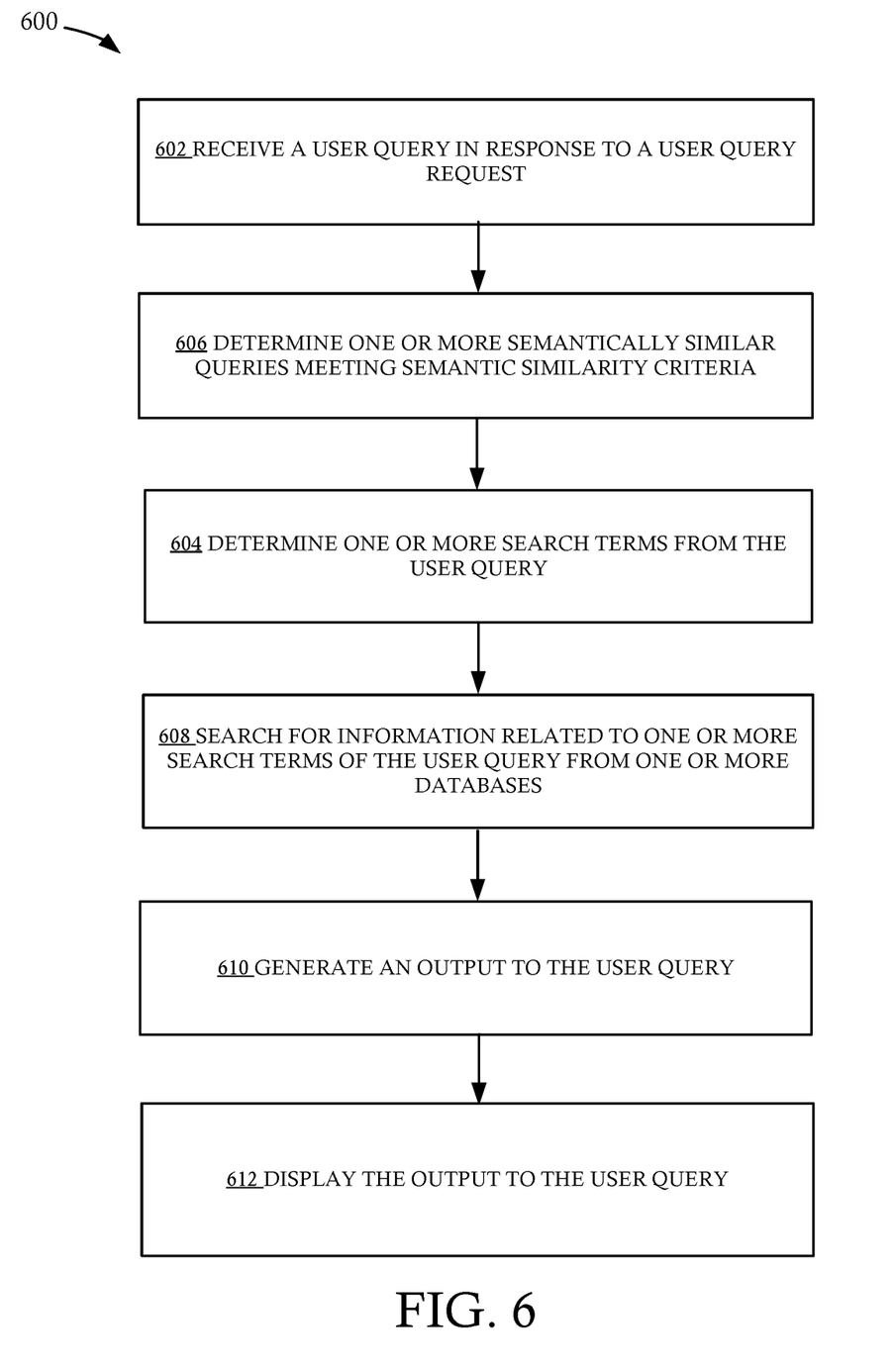
FIG. 6 is a flowchart illustrating a method of searching content using a machine learning model, in accordance with some embodiments.

FIG. 6 is a flowchart illustrating a machine-learning based search method 600, in accordance with some embodiments. At step 602, a user query 102 is received. The user query 102 may be received at a first user interface 300. In some embodiments, the user query 102 is in the form of natural language. In some embodiments, the user query 102 is in the form of a structured search. In some embodiments, the user query 102 is a combination of a natural language query and a structured search query. In some embodiments, the search system is configured to process a natural language query, a structured search query, and/or a query combining natural language and structured search.

At step 604, one or more semantically similar queries 104 meeting semantic similarity criteria are determined. The semantically similar queries 104 may be generated by one or more trained machine learning models (e.g., large language models) based on the user query 102. Generating the semantically similar queries 104 may be based on semantic similarity criteria defining a similarity threshold. For example, a lower similarity threshold may increase the number of semantically similar queries 104, and a higher similarity threshold may limit the number of semantically similar queries 104. More semantically similar queries 104 may be advantageous when the user query 102 is a query regarding an overview or otherwise high-level search of a topic. Fewer semantically similar queries 104 may be advantageous when the user query is specific in nature. For example, a specific user query may include a query regarding a single brand name drug for a specific population with regards to dosing. In this example, a lower similarity threshold may be selected to match the user's intention for a tailored search. The user query 102 and the semantically similar queries 104 may be compared to stored queries in a cache database. If a stored query matches, or is similar to, the user query 102 or the semantically similar query 104, the output associated with the stored query may be displayed to the user. If no stored query matches or is similar to the user query 102 or the semantically similar query 104, the user query 102 is passed to a query parser 114.

At step 606, one or more search terms are determined from the user query 102. The one or more terms may be determined using a query parser 114. The one or more search terms include one or more medical terms, such as being related to one or more drugs or one or more health indications. For example, a user query 102 may be directed to a recommended dosing for a specified drug for weight loss. In this example, weight loss is a health indication. The search terms may include or define a type of query. In some embodiments, the query parser 114 includes a machine learning model configured to determine the one or more search terms from the user query 102.

At step 608, one or more databases are searched to identify information related to the one or more search terms of the user query 102. A search may be performed using one or more trained machine learning models, such as, for example, one or more language models (e.g., large language models (LLM)). The language models may include generative pre-trained transformers. The one or more databases may provide grounding data for the LLMs. Grounding data can include contextually relevant information that was not in the training set for an LLM. For example, an LLM may search grounding data and summarize relevant data in response to the user query 102. Examples of databases may include, but are not limited to, DailyMed, PubMed, and/or other sources of publicly available data.

At step 610, an output is generated to the user query 102. In some embodiments, the output includes at least a portion of the information related to the one or more search terms, such as, for example, a summary of the information related to the one or more search terms. The information may be from a single source and/or may be from multiple sources. The summary may include information from documents in different databases. The output may include one or more citations associated with information related to the one or more search terms from the one or more databases. For example, an output may include a citation for each portion of information included in the output, where the citation references, links, and/or otherwise identifies the document from which the portion of information originated. In another example, an output may include one or more citations for a summary of the information, where each document and/or source that contributed to the summary may be cited. The citations may be incorporated and/or integrated with the output as endnotes, footnotes, a citation table, citation list, and/or other methods of providing citations to a user. At step 612, the output to the user query 102 is displayed via a user interface. In embodiments including citations, the citations may be provided inline to the output, as an endnote, footnote, appendix, or otherwise not in line with the output, and/or using any other suitable format. The one or more citations may provide a programmatic link to the source document, e.g., the specific portion of the source document related to the output.

Although the methods described above are with reference to the illustrated flowcharts, it will be appreciated that many other ways of performing the acts associated with the methods may be used. For example, the order of some operations may be changed, and some of the operations described may be optional.

In addition, the methods and system described herein may be at least partially embodied in the form of computer-implemented processes and apparatus for practicing those processes. The disclosed methods may also be at least partially embodied in the form of tangible, non-transitory machine-readable storage media encoded with computer program code. For example, the steps of the methods may be embodied in hardware, in executable instructions executed by a processor (e.g., software), or a combination of the two. The media may include, for example, RAMs, ROMs, CD-ROMs, DVD-ROMs, BD-ROMs, hard disk drives, flash memories, or any other non-transitory machine-readable storage medium. When the computer program code is loaded into and executed by a computer, the computer becomes an apparatus for practicing the method. The methods may also be at least partially embodied in the form of a computer into which computer program code is loaded or executed, such that, the computer becomes a special purpose computer for practicing the methods. When implemented on a general-purpose processor, the computer program code segments configure the processor to create specific logic circuits.

Although the subject matter has been described in terms of exemplary embodiments, it is not limited thereto. Rather, the appended claims should be construed broadly, to include other variants and embodiments, which may be made by those skilled in the art.

What is claimed is:

1. A system for searching a database structure using semantically and categorically similar queries and a hybrid retrieval process, comprising:
 a non-transitory memory;
 a processor communicatively coupled to the non-transitory memory, wherein the processor is configured to read a set of instructions to:
  train at least one semantic similarity model configured to identify a set of semantically similar queries to a received input query based on semantic similarity criteria;
  train at least one hybrid retrieval model configured to apply a hybrid retrieval search process based on one or more search terms;
  receive, at a first user interface, a user query;
  determine, by the at least one semantic similarity model and the user query, one or more semantically similar search queries meeting the semantic similarity criteria;
  select, using a query parser, one or more search terms of the user query, wherein the one or more search terms satisfy search term criteria including a query category;
  in accordance with a determination that the user query and the one or more semantically similar search queries have not been previously searched:
   search, using the at least one hybrid retrieval model, for information related to the one or more search terms of the user query from one or more databases;
  generate, based on the information related to the one or more search terms, an output to the user query, wherein the output to the user query includes:
   at least a portion of the information related to the one or more search terms; and
   one or more citations associated with the information related to the one or more search terms from the one or more databases; and
  display, at the first user interface, the output to the user query.

2. The system of claim 1, wherein the one or more search terms includes one or more of a drug name, a query type, an indication, or a specific population.

3. The system of claim 1, wherein the processor is further configured, in accordance with a determination that none of the one or more search terms satisfy the search term criteria, to read the set of instructions to:
 generate an error to the user query requesting a different user query; and
 displaying, at the first user interface, the error to the user query.

4. The system of claim 1, wherein the query parser selects at least one machine learning model of the one or more machine learning models are used to search, and wherein the query parser selects at least one database of the one or more databases the at least one machine learning model searches.

5. The system of claim 4, wherein selecting the at least one machine learning model and the at least one database are based on the one or more search terms.

6. The system of claim 5, wherein selecting the at least one machine learning model and the at least one database are based on the one or more search terms matching specified search routing criteria.

7. The system of claim 4, wherein the query parser includes a parsing machine learning model distinct from the one or more machine learning models for searching.

8. The system of claim 1, wherein the processor is further configured, in accordance with a determination that a respective search term of the one or more search terms is a respective misspelled search term, to read the set of instructions to
replace the respective misspelled search term with a respective correctly spelled search term; and
search, using the at least one hybrid retrieval model and based on the one or more search terms of the user query, wherein the respective search terms of one or more search terms have been replaced with the respective correctly spelled search term, for information related to the one or more search terms from the one or more databases.

9. The system of claim 1, wherein the hybrid retrieval search process includes spelling correction of the user query and one or more search filters based on the user query.

10. The system of claim 9, wherein the hybrid retrieval search process includes finding a specified number of relevant snippets of text to inject into the user query.

11. The system of claim 9, wherein the hybrid retrieval search process includes determining a specified brand into the user query, wherein the specified brand is based on the user query.

12. The system of claim 1, wherein the processor is further configured to read the set of instructions to process one or more documents of the one or more databases, wherein the processing includes parsing, chunking, embedding, and/or storing the one or more documents to a cache database.

13. The system of claim 12, wherein the processor is further configured to read the set of instructions to store the user query to the cache database.

14. The system of claim 12, wherein the processor is further configured to read the set of instructions to store the output to the user query to the cache database.

15. The system of claim 12, wherein the processor is further configured to read the set of instructions to store one or more suggested follow-up user queries to the cache database.

16. The system of claim 1, wherein searching for information related to the one or more search terms from the one or more databases includes in accordance with a determination that the user query is similar to a previous user query stored in a cache database, search a cache database for the previous user query and an associated previous output to the previous user query.

17. The system of claim 1, wherein the processor is further configured to read the set of instructions to, in accordance with a determination that the user query is not similar to a previous user query stored in a cache database, provide the one or more search terms of the user query to the at least one hybrid retrieval model.

18. The system of claim 1, wherein a respective machine learning model of the one or more machine learning models is trained to process information from a respective database of the one or more databases.

19. A computer-implemented method for searching a database structure using semantically and categorically similar queries and a hybrid retrieval process, comprising:
training at least one semantic similarity model configured to identify a set of semantically similar queries to a received input query based on semantic similarity criteria;
training at least one hybrid retrieval model configured to apply a hybrid retrieval search process based on one or more search terms;
receiving, at a first user interface, a user query in response to a user query request, wherein the user query includes one or more search terms;
determining, by the at least one semantic similarity model and the user query, one or more semantically similar search queries meeting the semantic similarity criteria;
selecting, using a query parser, one or more search terms of the user query, wherein the one or more search terms satisfy search term criteria including a query category;
searching, using the at least one hybrid retrieval model and based on the one or more search terms of the user query, for information related to the one or more search terms from one or more databases;
generating, based on the information related to the one or more search terms, an output to the user query, wherein the output to the user query includes:
at least a portion of the information related to the one or more search terms; and
one or more citations associated with the information related to the one or more search terms from the one or more databases; and
displaying, at the first user interface, the output to the user query.

20. A non-transitory computer readable medium having instructions stored thereon, wherein the instructions, when executed by at least one processor, cause at least one device to perform operations comprising:
training at least one semantic similarity model configured to identify a set of semantically similar queries to a received input query based on semantic similarity criteria;
training at least one hybrid retrieval model configured to apply a hybrid retrieval search process based on one or more search terms;
receiving, at a first user interface, a user query in response to a user query request, wherein the user query includes one or more search terms;
determining, by the at least one semantic similarity model and the user query, one or more semantically similar search queries meeting the semantic similarity criteria;
selecting, using a query parser, one or more search terms of the user query, wherein the one or more search terms satisfy search term criteria including a query category;
searching, using the at least one hybrid retrieval model and based on the one or more search terms of the user query, for information related to the one or more search terms from one or more databases;
generating, based on the information related to the one or more search terms, an output to the user query, wherein the output to the user query includes:
at least a portion of the information related to the one or more search terms; and
one or more citations associated with the information related to the one or more search terms from the one or more databases; and
displaying, at the first user interface, the output to the user query.

* * * * *